United States Patent [19]

Meilland

[11] Patent Number: Plant 7,621

[45] Date of Patent: Aug. 20, 1991

[54] ROSE PLANT — MEIDANCLAR VARIETY

[75] Inventor: Alain A. Meilland, Antibes, France

[73] Assignee: The Conard-Pyle Company, West Grove, Pa.

[21] Appl. No.: 508,710

[22] Filed: Apr. 3, 1990

[51] Int. Cl.[5] ..... A01H 5/00
[52] U.S. Cl. ..... Plt./9
[58] Field of Search ..... Plt. 9, 7

*Primary Examiner*—Howard J. Locker

*Attorney, Agent, or Firm*—Burns, Doane, Swecker & Mathis

[57] ABSTRACT

A new and distinct variety of rose plant of the Miniature Class is provided which abundantly forms attractive long lasting very double blossoms. The blossoms are fuschia purple in coloration. The plant is bushy, forms vigorous dark green and glossy vegetation, and is well adapted for use as ornamentation in parks and gardens. Additionally, the plant is not particularly affected by crytogamic diseases.

1 Drawing Sheet

SUMMARY OF THE INVENTION

The new variety of the present invention came into being as a spontaneous sport of the Meilarco variety (U.S. Plant Pat. No. 6,170) of unknown causation. The original plant of the new variety was discovered to form blossoms having a distinctive fuschia purple coloration unlike the pastel romantic pink blossom coloration of the Meilarco variety. The other important characteristics of the new variety such as growth habit, foliage appearance, and blossom configuration were found to be substantially identical to those of the Meilarco variety. Had the new variety not been discovered by me and asexually reproduced, it would have been lost to mankind.

The new variety has undergone intensive study and observation and has been found to consistently display its distinctive characteristics.

It was found that the new variety of Miniature rose plant of the present invention possesses the following combination of characteristics:

(a) forms in abundance attractive very double long lasting blossoms which are fuschia purple in coloration;
(b) forms very vigorous vegetation having dark green glossy foliage;
(c) exhibits a bushy growth habit, and
(d) is not particularly affected by crytogamic diseases.

The new variety well meets the needs of the horticultural industry for many usages. It is particularly well-suited for use as attractive ornamentation for parks and gardens.

The new variety has been found to undergo asexual propagation by a number of routes, including budding, grafting, cuttage, etc. The characteristics of the new variety have been found to be stable and to be strictly transmissible by such asexual propagation from one generation to another.

The new variety has been named the Meidanclar variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were one year of age and were observed during October while growing on their own roots in greenhouses at Le Cannet des Maures, Var, France.

DETAILED DESCRIPTION

Figures 1, 2, 3, 4, 5, 6, 7, 8, 9, 10, 11, 12, 13, 14, 15, 16:
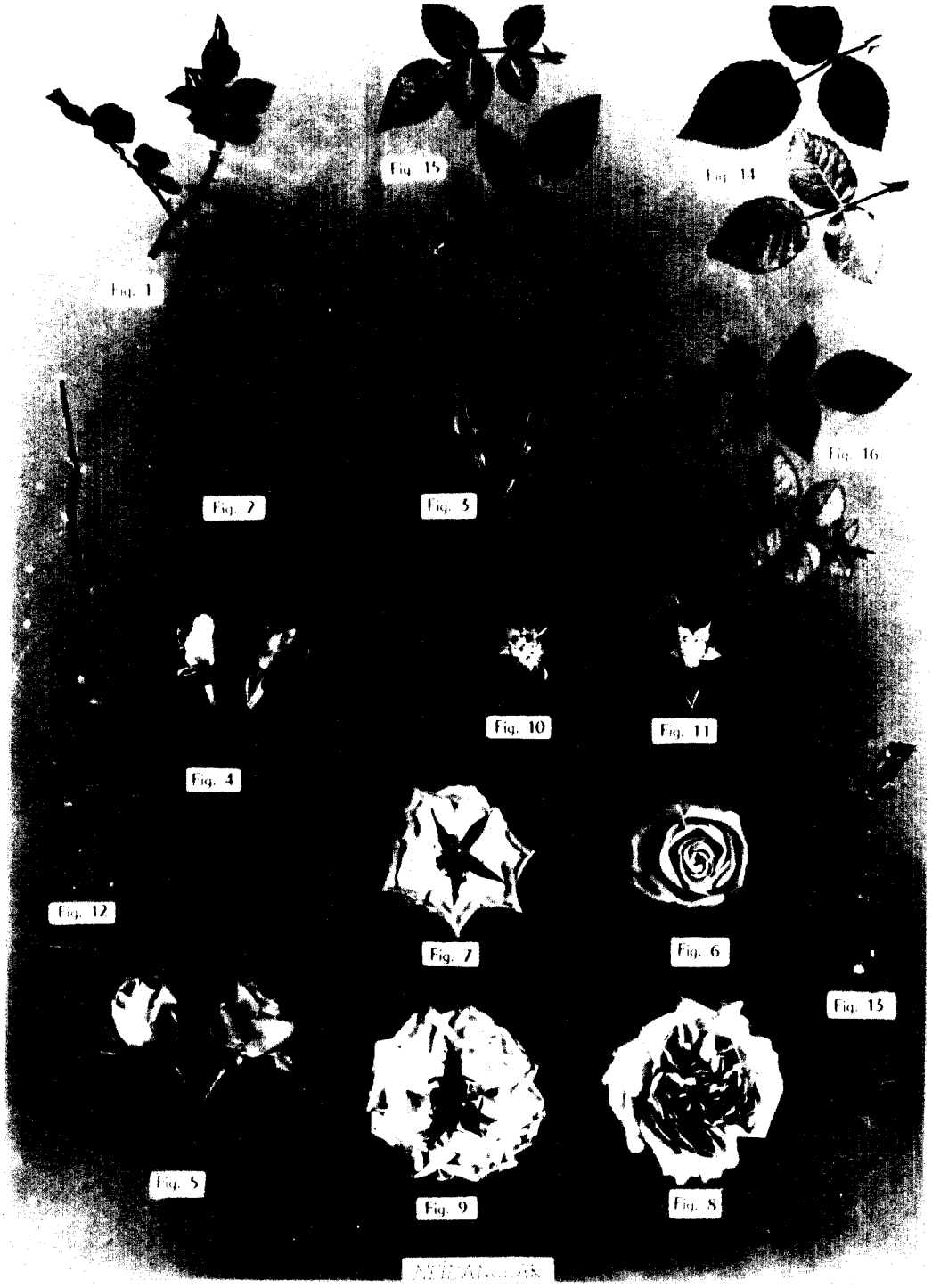
FIG. 1 illustrates a specimen of a young shoot.
FIG. 2 illustrates specimens of two floral buds before the opening of the sepals.
FIG. 3 illustrates specimens of two floral buds at the opening of the sepals.
FIG. 4 illustrates specimens of two floral buds at the opening of the petals.
FIG. 5 illustrates a specimen of two flowers in the course of opening.
FIG. 6 illustrates a specimen of a flower in the course of opening — plan view — obverse.
FIG. 7 illustrates a specimen of a flower in the course of opening — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of leaves with three leaflets with the upper surface being shown on the top and the under surface being shown on the bottom.
FIG. 15 illustrates specimens of leaves with five leaflets with the under surface being shown on the top and the upper surface being shown on the bottom.
FIG. 16 illustrates specimens of leaves with seven leaflets with the upper surface being shown on the top and the under surface being shown on the bottom.

The chart used in the identification of the colors is that of The Royal Horticultural Society (R.H.S. Colour Chart). The terminology which precedes reference to the chart has been added to indicate the corresponding colors in common terms. The description is based on one year old specimens of the new variety which are observed during October while growing on their own roots in greenhouses at Le Cannet des Maures, Var, France.

Class: Miniature.

Plant:

*Height.*—Approximately 30 cm. on average.

*Habit.*—Bushy.

Branches:

*Color.*—Young stems: lettuce green, Yellow-Green Group 144A, sometimes stained with reddish coloration. Adult wood: light green, Yellow-Green Group 146B.

*Thorns.*—Size: medium to large. Quantity: average. Color: pinkish on young stems and pinkish green changing to light tan on adult wood.

Leaves:

*Petioles.*—Upper surface: striped, reddish green on young foliage and light green on adult foliage with glandular edges. Under surface: light green with a few crooked prickles.

*Stipules.*—Adnate, pectinate, fairly wide and linear.

*Leaflets.*—Number: 3, 5 (most often), and sometimes 7. Shape: elliptic. Serration: single and regular. Texture: leathery. General appearance: dense and glossy dark green foliage. Color (young foliage): Upper surface: lettuce green, Yellow-Green Group 144A, edged with reddish coloration and more or less suffused with reddish brown coloration. Under surface: lettuce green, Yellow-Green Group 144A, and edged with reddish coloration. Color (adult foliage): Upper surface: glossy dark green, Yellow-Green Group 147A. Under surface: medium green, Yellow-Green Group 147B.

Inflorescence:

*Number of flowers.*—Approximately 1 to 5 per stem.

*Peduncle.*—Straight, rigid, smooth, medium green in coloration, its length is approximately 6 cm. on average.

*Sepals.*—Upper surface: tomentose and greenish in coloration. Under surface: medium green, smooth, and the outer sepals have edges which are very appendiculated.

*Buds.*—Shape: ovoid. Length: approximately 2 cm. on average. Size: fairly large for the Miniature Class. Color upon opening: Upper surface: fuschia purple, Red-Purple Group 67C. Under surface: fuschia purple, Red-Purple Group 67C.

*Flower.*—Form: slightly globular, changing to cup-like, very double. Diameter: approximately 6 to 7 cm. on average. Color (when opening begins): Upper surface: fuschia purple, Red-Purple Group 67C. Under surface: fuschia purple, Red-Purple Group 67C. Color (when blooming): Upper surface: fuschia purple, Red-Purple Group 67C. Under surface: fuschia purple, Red-Purple Group 67D. Color (at end of blooming): Upper surface: fuschia purple, Red-Purple Group 67C. Under surface: fuschia purple, Red-Purple Group 67D. Fragrance: none. Lasting quality: long. Petal number: approximately 85 to 95 on average. Petal texture: consistent. Petal drop: drop off clearly. Stamens and pistils: young plants commonly exhibit a vegetative blossom center where a few light yellow stamens are present, and older plants commonly exhibit only a very few stamens and pistils which are each light yellow in coloration.

Development:

*Vegetation.*—Vigorous.

*Blooming.*—Abundant.

*Aptitude to bear fruits.*—Poor.

*Resistance to frost.*—Good.

*Resistance to diseases.*—Good.

I claim:

1. A new and distinct variety of Miniature rose plant characterized by the following combination of characteristics:

(a) forms in abundance attractive very double long lasting blossoms which are fuschia purple in coloration;

(b) forms vigorous vegetation having dark green glossy foliage;

(c) exhibits a bushy growth habit, and (d) is not particularly affected by cryptogamic diseases;

substantially as herein shown and described.

* * * * *